US010251535B2

(12) United States Patent
Saito et al.

(10) Patent No.: US 10,251,535 B2
(45) Date of Patent: Apr. 9, 2019

(54) FLEXIBLE TUBE AND INSERTION APPARATUS

(71) Applicant: OLYMPUS CORPORATION, Hachioji-shi, Tokyo (JP)

(72) Inventors: Kenichiro Saito, Tachikawa (JP); Takahiro Kishi, Yokohama (JP); Naoyuki Hoshi, Aizuwakamatsu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/611,443

(22) Filed: Jun. 1, 2017

(65) Prior Publication Data

US 2017/0265720 A1   Sep. 21, 2017

Related U.S. Application Data

(63) Continuation of application No. PCT/JP2015/083800, filed on Dec. 1, 2015.

(30) Foreign Application Priority Data

Dec. 2, 2014   (JP) .................................. 2014-244359

(51) Int. Cl.
   *A61B 1/005*   (2006.01)
   *G02B 23/24*   (2006.01)
   (Continued)

(52) U.S. Cl.
   CPC ............ *A61B 1/0055* (2013.01); *A61B 1/005* (2013.01); *A61B 1/0051* (2013.01);
   (Continued)

(58) Field of Classification Search
   CPC ............ A61B 1/00064; A61B 1/00078; A61B 2017/00305; A61M 25/0053;
   (Continued)

(56) References Cited

U.S. PATENT DOCUMENTS 5,549,542 A * 8/1996 Kovalcheck ......... A61B 1/0052
                                                        600/146
5,997,487 A * 12/1999 Kolehmainen ... A61M 25/0009
                                                        600/585
(Continued)

FOREIGN PATENT DOCUMENTS

JP      S63-249536 A    10/1988
JP      2002-65592 A    3/2002
(Continued)

OTHER PUBLICATIONS

Oct. 4, 2016 Office Action issued in Japanese Patent Application No. 2016-550887.
(Continued)

*Primary Examiner* — Ryan Henderson
*Assistant Examiner* — Aaron B Fairchild
(74) *Attorney, Agent, or Firm* — Oliff PLC

(57) ABSTRACT

A flexible tube includes a first outer layer covering an outer side of a closely-wound region; a second outer layer forming a second flexible portion which is more difficult to bend than the first flexible portion; a third outer layer covering an outer side of the sparsely-wound region, and forming a third flexible portion which is as difficult to bend as the second flexible portion, or more difficult to bend than the second flexible portion; and a fourth outer layer arranged consecutively between the second and third outer layers to cover the outer side of a boundary position of the closely-wound region and the sparsely-wound region, and reducing a difference in bending difficulty/bending easiness at the boundary position.

10 Claims, 8 Drawing Sheets

(51) Int. Cl.
*A61M 25/00* (2006.01)
*A61B 1/00* (2006.01)
*F16L 11/10* (2006.01)

(52) U.S. Cl.
CPC ...... *A61B 1/00064* (2013.01); *A61B 1/00071* (2013.01); *A61B 1/00078* (2013.01); *A61M 25/005* (2013.01); *A61M 25/0053* (2013.01); *A61M 25/0054* (2013.01); *F16L 11/10* (2013.01); *G02B 23/2476* (2013.01); *A61B 1/0057* (2013.01)

(58) Field of Classification Search
CPC ........... A61M 25/0054; A61M 25/0147; F16L 11/081; F16L 11/082; F16L 11/083; F16L 11/10; F16L 11/16
See application file for complete search history.

(56) References Cited

U.S. PATENT DOCUMENTS

| | | | |
|---|---|---|---|
| 2002/0028984 A1 | 3/2002 | Hayakawa et al. | |
| 2009/0023989 A1* | 1/2009 | Honda | A61B 1/00133 600/106 |
| 2009/0318764 A1* | 12/2009 | Yoshimoto | A61B 1/005 600/140 |
| 2013/0112457 A1* | 5/2013 | Kitagawa | A61B 1/0056 174/68.3 |
| 2013/0144126 A1* | 6/2013 | Iede | A61B 1/0055 600/139 |
| 2013/0331651 A1* | 12/2013 | Iede | A61B 1/0055 600/140 |
| 2014/0155697 A1* | 6/2014 | Iede | A61B 1/0055 600/139 |
| 2014/0188081 A1 | 7/2014 | Saito et al. | |
| 2016/0249786 A1* | 9/2016 | Saito | G02B 23/2476 600/140 |
| 2016/0249788 A1* | 9/2016 | Saito | A61B 1/0055 600/140 |
| 2017/0215712 A1* | 8/2017 | Hoshi | A61B 1/01 |
| 2017/0254447 A1* | 9/2017 | Saito | F16L 11/10 |
| 2017/0261136 A1* | 9/2017 | Saito | F16L 11/10 |
| 2018/0042458 A1* | 2/2018 | Araki | A61B 1/0055 |

FOREIGN PATENT DOCUMENTS

| | | |
|---|---|---|
| JP | 2007-236472 A | 9/2007 |
| WO | 2013/168552 A1 | 11/2013 |
| WO | 2015/083644 A1 | 6/2015 |

OTHER PUBLICATIONS

Feb. 23, 2016 Search Report issued in International Patent Application No. PCT/JP2015/083800.

Jun. 15, 2017 International Preliminary Report on Patentability received in International Application No. PCT/JP2015/083800.

* cited by examiner

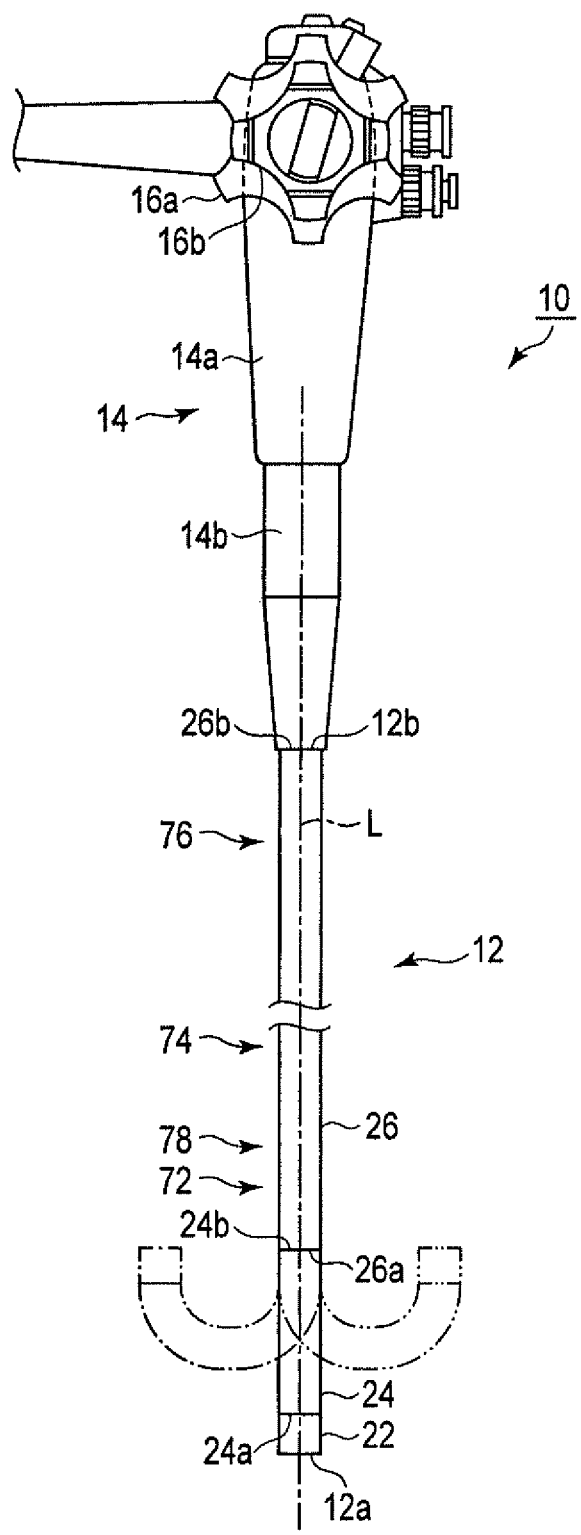
F I G. 1

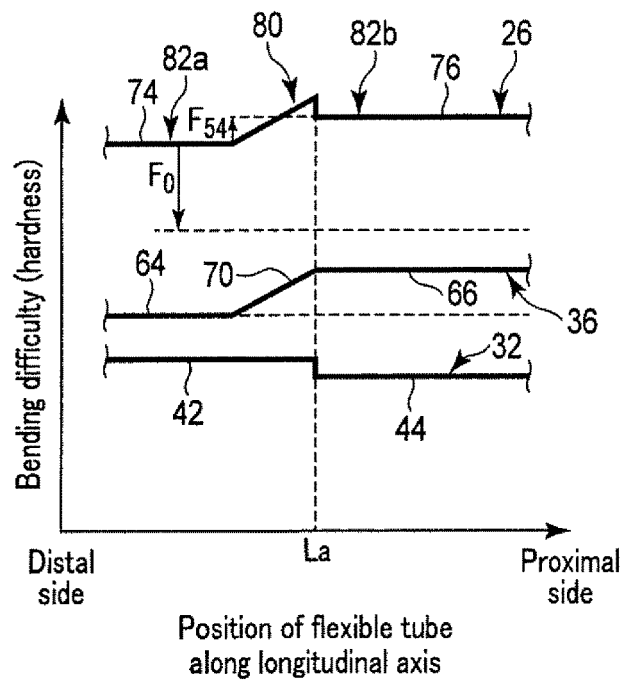
F I G. 5
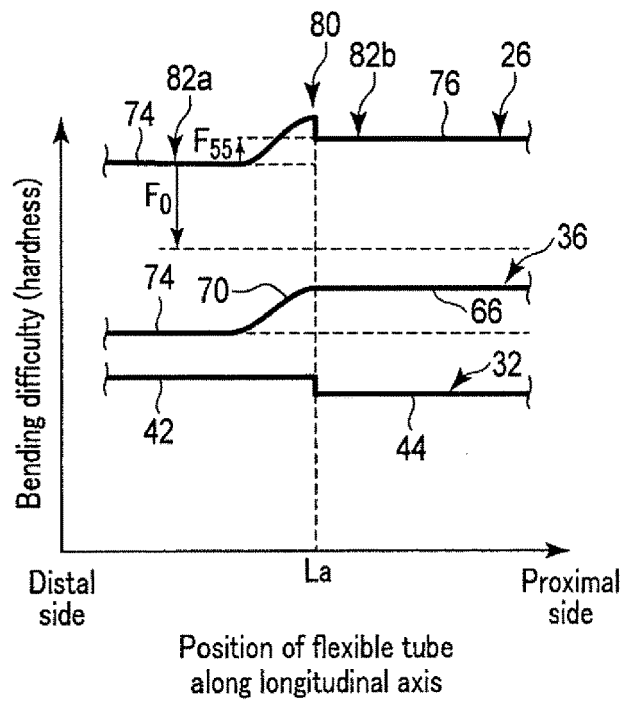
F I G. 6

FLEXIBLE TUBE AND INSERTION APPARATUS

CROSS-REFERENCE TO RELATED APPLICATIONS

This application is a Continuation application of PCT Application No. PCT/JP2015/083800, filed Dec. 1, 2015 and based upon and claiming the benefit of priority from prior Japanese Patent Application No. 2014-244359, filed Dec. 2, 2014, the entire contents of all of which are incorporated herein by reference.

BACKGROUND OF THE INVENTION

1. Field of Invention

The present invention relates to a flexible tube used for an insertion apparatus of an endoscope, etc. and an insertion apparatus including the flexible tube.

2. Description of Related Art

Jpn. Pat. Appln. KOKAI Publication No. 2007-236472, for example, describes an example of combining a plurality of tubes with different bending difficulties (hardness) along a longitudinal axis to form a catheter. This catheter is formed to be continuously more flexible at the distal side in comparison with the proximal side.

BRIEF SUMMARY OF THE INVENTION

According to one aspect of the present invention, a flexible tube includes: a closely-wound region which is arranged along a longitudinal axis defined by a distal end and a proximal end, and which includes a closely-wound portion to which a tight contact force where adjacent parts of a wire member adjacent along the longitudinal axis come in a tight contact state with each other is applied; a sparsely-wound region which is arranged consecutively on a proximal side of the closely-wound region along the longitudinal axis, and which is formed so that the adjacent parts of the wire member adjacent along the longitudinal axis are separated from each other to be bent easier than the closely-wound portion; a first outer layer which covers an outer side of the closely-wound region, and which forms a first flexible portion in cooperation with the closely-wound region; a second outer layer which is positioned closer to the proximal side than the first outer layer along the longitudinal axis, and which forms a second flexible portion which is more difficult to bend than the first flexible portion in cooperation with the closely-wound region; a third outer layer which covers an outer side of the sparsely-wound region, and which forms a third flexible portion which is more difficult to bend than the first flexible portion, and which is as difficult to bend as the second flexible portion, or more difficult to bend than the second flexible portion in cooperation with the sparsely-wound region; and a fourth outer layer which is arranged consecutively between the second and third outer layers to cover the outer side of a boundary position of the closely-wound region and the sparsely-wound region, and which reduces a difference in bending difficulty/bending easiness at the boundary position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of an endoscope to be used as an insertion apparatus according to a first embodiment to an eighth embodiment.

FIG. 5 is a schematic view showing a bending difficulty with respect to a position along a longitudinal axis of a helical tube and an outer tube of a flexible tube of an insertion section of an endoscope according to the fourth embodiment, together with a bending difficulty of the flexible tube obtained by adding the bending difficulties of the helical tube and the outer tube together by a principle of superposition.

FIG. 6 is a schematic view showing a bending difficulty with respect to a position along a longitudinal axis of a helical tube and an outer tube of a flexible tube of an insertion section of an endoscope according to the fifth embodiment, together with a bending difficulty of the flexible tube obtained by adding the bending difficulties of the helical tube and the outer tube together by a principle of superposition.

DETAILED DESCRIPTION OF THE INVENTION

Figure 2A:
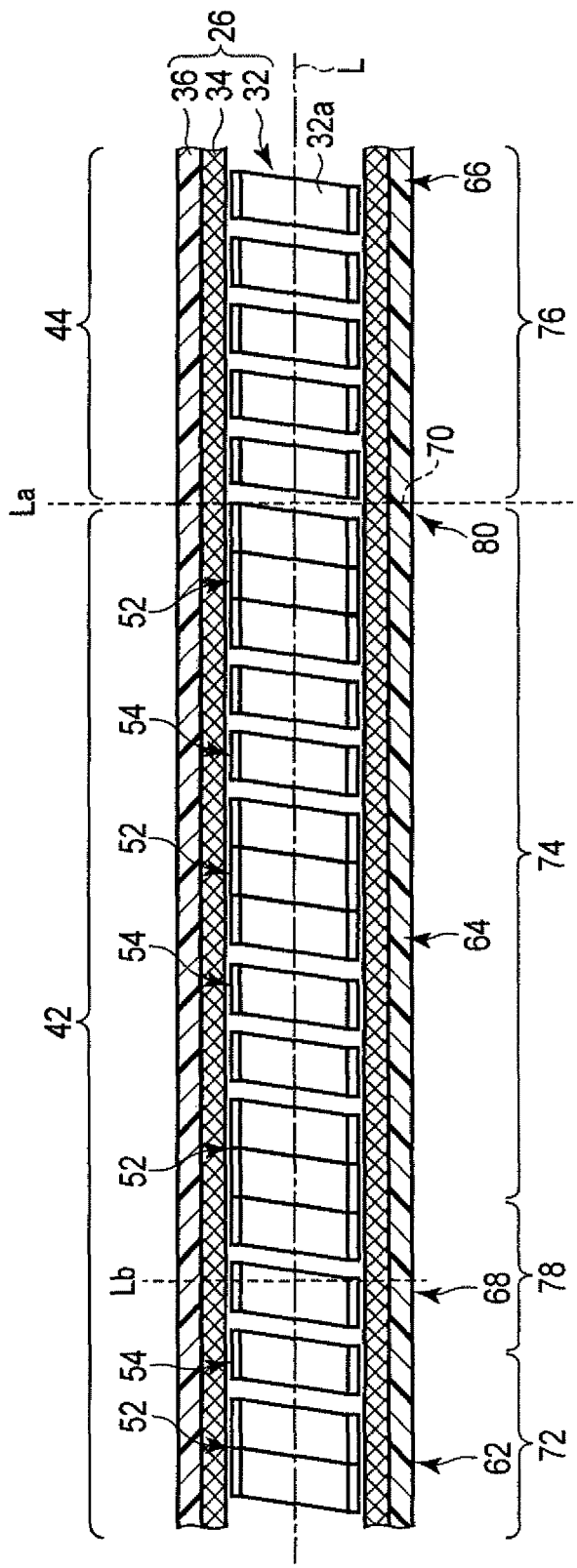
FIG. 2A is a schematic longitudinal sectional view of a part of a flexible tube of an insertion section of the endoscope according to the first embodiment.

Hereinafter, embodiments for implementing the present invention will be explained with reference to the drawings.

The first embodiment will be explained using FIG. 1 to FIG. 2B.

An insertion apparatus 10 according to the present embodiment will be explained assuming that it is, for example, a medical endoscope. The insertion apparatus 10 is not only preferred as being a medical endoscope, but also as being an industrial endoscope, or an insertion instrument such as a catheter which does not have an illumination optical system or an observation optical system.

As shown in FIG. 1, the insertion apparatus 10 according to the present embodiment includes an insertion section 12 including a distal portion 12a and a proximal portion 12b, and a grip section (operation section) 14 located at the proximal portion 12b of the insertion section 12. The grip section 14 includes a grip section main body 14a gripped by a user and a protection hood 14b. The proximal portion 12b of the insertion section 12 is coupled to the grip section 14 through the protection hood 14b, which prevents the insertion section 12 from being bent, such as buckled, at the proximal portion 12b thereof.

The distal portion 12a and proximal portion 12b of the insertion section 12 or the distal end 26a and proximal end 26b of a flexible tube 26 mentioned below define a longitudinal axis L as a central axis. The insertion section 12 includes, from its distal end to its proximal end, a distal rigid portion 22, a bending portion 24, and a flexible tube 26. The distal end 24a of the bending portion 24 is coupled to the distal rigid portion 22. The distal end 26a of the flexible tube 26 is coupled to the proximal end 24b of the bending portion 24. The proximal end 26b of the flexible tube 26 is coupled to the protection hood 14b of the grip section 14.

The bending portion 24 can be bent, for example, in four directions by operating the knobs 16a and 16b of the grip section main body 14a.

As shown in FIG. 2A, the flexible tube 26 includes a helical tube 32, a cylindrical and net-like braid 34, and a cylindrical outer tube 36 in a radial direction with respect to the central axis (longitudinal axis) L, from the inner side to the outer side thereof. The braid 34 is not indispensable. It is also preferable to have the outer side of the helical tube 32 covered directly by the outer tube 36.

The helical tube 32 is formed by winding a wire member 32a, which is made of, for example, a metal such as stainless steel and is an elongated band, around the longitudinal axis L. It is desirable that the helical tube 32 is formed to have constant or essentially constant outer diameter and inner diameter from its distal end to proximal end. The helical tube 32 is a spiral tubular member that is difficult to bend in a bending direction departing from the longitudinal axis L (for example, a direction perpendicular to the longitudinal axis L), and has resiliency tending to return to its original state from a bent state.

The helical tube 32 is arranged on the longitudinal axis L and, from the distal end towards the proximal end along the longitudinal axis, includes a closely-wound region (a region with high resiliency) 42 and a sparsely-wound region (a region with usual resiliency which has lower resiliency than the region with high resiliency) 44 coupled to the proximal side of the closely-wound region 42. The sparsely-wound region 44 is arranged continuously at the proximal side of the closely-wound region 42, and is formed to be bent easier than the closely-wound region 42. The closely-wound region 42 is formed to have high resiliency, which causes the helical tube 32 to return to an essentially linear state from a bent state more easily than the sparsely-wound region 44.

It is favorable that, for example, when the insertion section 12 is inserted into a deep part of a large intestine from an anus, the length of the closely-wound region 42 along the longitudinal axis L is formed about the same as or longer than the length when the large intestine is made essentially linear.

In the case where the insertion apparatus 10 is an endoscope used for the large intestine, it is favorable that the length (distance) between the distal end 26a of the flexible tube 26 and the proximal end of a third flexible portion 76 explained later on is approximately 700 mm or so, and the length (distance) between the distal end 26a of the flexible tube 26 and the distal end of a second flexible portion 74 explained later on is desirably approximately 300 mm or so.

The length of the closely-wound region 42 along the longitudinal axis L, that is, a distance (length) La between the distal end 26a of the flexible tube 26 and the proximal end of the closely-wound region 42 (refer to FIG. 2A, FIG. 2B, and FIG. 3), is set as appropriate in accordance with a body portion to be examined. The length of the sparsely-wound region 44 along the longitudinal axis L can also be set as appropriate.

The closely-wound region 42 includes a plurality of closely-wound portions 52 and a plurality of sparsely-wound portions 54 which are consecutively and alternately arranged along the longitudinal axis L. In other words, each sparsely-wound portion 54 is located between a plurality of closely-wound portions 52. In the case where the closely-wound portions 52 are three in number, the sparsely-wound portions 54 are at least two in number. That is, it is also preferable that there are two or more sparsely-wound portions 54.

It is desirable to have the sparsely-wound portion 54 arranged at the most distal end of the closely-wound region 42. On the other hand, it is desirable to have the closely-wound portion 52 arranged at the most proximal end of the closely-wound region 42. It is desirable to have each closely-wound portion 52 formed longer than each sparsely-wound portion 54 along the longitudinal axis L. That is, in the present embodiment, in the closely-wound region 42, it is desirable to have the sum of the lengths of the closely-wound portions 52 along the longitudinal axis L larger than the sum of the lengths of the sparsely-wound portions 54 along the longitudinal axis L.

A tight contact force (≤initial tension) is applied to each closely-wound portion 52, thus enabling adjacent parts of the wire member 32a adjacent with each other along the longitudinal axis L to come into a tight contact state with each other by the initial tension that brings the adjacent parts of the wire member 32a adjacent along the longitudinal axis L in a tight contact state. The initial tension (tight contact force) to be applied here can be adjusted as appropriate, for example, by how the wire member 32a is wound. Here, to simplify the explanation, it is assumed that the tight contact force that is based on the initial tension between the adjacent parts of the wire member 32a in the closely-wound portions 52 is essentially constant at any position.

The tight contact force of the adjacent parts of the wire member 32a can be varied by changing the structure of the winding or changing the width and plate thickness, etc. of the wire member 32a themselves along the longitudinal axis as appropriate.

When the longitudinal axis L of the closely-wound portion 52 is arranged vertically, the tight contact force maintains a state where the adjacent parts of the wire member 32a of the closely-wound portion 52 are in tight contact against the force of gravity, and no gap is provided between the adjacent parts of the wire member 32a. If an external force is applied against the longitudinal axis L of the closely-wound portion 52 in a state where the longitudinal axis L is arranged, for example, horizontally, a gap between the adjacent parts of the wire member 32a will not be formed until the external force reaches a force that cancels out the tight contact force. In this manner, the closely-wound portion 52 is prevented from being deflected. If the external force applied against the longitudinal axis L exceeds the tight contact force between the adjacent parts of the wire member 32a, a gap will be produced between the tightly contacted adjacent parts of the wire member 32a of the closely-wound portion 52. As a result, the closely-wound portion 52 will be deflected. Therefore, due to the tight contact force applied to the adjacent parts of the wire member 32a adjacent along the longitudinal axis L, the closely-wound portion 52 has a large bending rigidity before the closely-wound portion 52 begins to bend. After the closely-wound portion 52 begins to bend and is deprived of the tight contact force, it bends in accordance with the spring constant of the helical tube 32. That is, the magnitude of the tight contact force applied to the adjacent parts of the wire member 32a corresponds to the difficulty of bending the helical tube 32. Therefore, when inserting the insertion section 12 into an appropriate passage, once the closely-wound portion 52 of the flexible tube 26 starts bending, the flexible tube 26 can be bent as if the closely-wound portion 52 does not exist.

In the state where the closely-wound portion 52 is bent, the tight contact force between the adjacent parts of the wire member 32a along the longitudinal axis L of the closely-wound portion 52 helps exhibit the resiliency enabling the closely-wound portion 52 to return to its original state. That is, the magnitude of the tight contact force applied to the adjacent parts of the wire member 32a corresponds to the resiliency of the helical tube 32. In particular, in the case where the gaps between the adjacent parts of the wire member 32a of the closely-wound portion 52 are narrow (in the case where the radius of curvature of the closely-wound portion 52 is large in the bent state), the closely-wound portion 52 exhibits a higher resiliency than each sparsely-wound portion 54.

In each sparsely-wound portion 54, the adjacent parts of the wire member 32a adjacent in a direction along the longitudinal axis L are separated from each other by given intervals (pitches). That is, in the sparsely-wound portion 54, the adjacent parts of the wire member 32a are separate from each other, and a tight contact force is not applied between the adjacent parts of the wire member 32a. Therefore, the sparsely-wound portion 54 is formed to be bent easier in a direction departing from the longitudinal direction L (for example, a perpendicular direction) than the closely-wound portion 52. In the sparsely-wound portion 54, the intervals at which the adjacent parts of the wire member 32a are arranged need not be constant; the intervals may be shortened or lengthened, depending upon the portions.

Each sparsely-wound portion 54 has spring characteristics. Therefore, each sparsely-wound portion 54 exhibits appropriate resiliency by which each sparse winding portion 54 attempts to return to the original state from the bent state. Unlike the adjacent parts of the wire member 32a of the closely-wound portion 52, a tight contact force is not applied to the adjacent parts of the wire member 32a of each sparsely-wound portion 54. Therefore, the resiliency of each sparsely-wound portion 54 is lower than that of the closely-wound portion 52.

Since the adjacent parts of the wire member 32a of the sparsely-wound portion 54 are separated from each other, when the helical tube 32 is arranged horizontally, the gravity on the end part of the helical tube 32 causes the helical tube 32 to easily bend at such part and easily maintain the bent state. In contrast, the adjacent parts of the wire member 32a of the closely-wound portion 52 are in tight contact with each other. Therefore, when the helical tube 32 is arranged horizontally, it is difficult to be bent by the gravity on the end part of the helical tube 32; even if it is bent, it easily returns to an essentially straight state.

The flexible tube 26 is formed to maintain its overall length by the outer tube 36. That is, the outer tube 36 defines the overall length of the flexible tube 26, and the overall length of the helical tube 32 is prevented from varying. When an external force is applied to the closely-wound region 42 from a direction departing from the longitudinal axis L (for example, a direction perpendicular to the longitudinal axis L), the closely-wound region 42 is bent as the sparsely-wound portion 54 mainly functions as a buffer. That is, the gaps between the adjacent parts of the wire member 32a of the sparsely-wound portion 54 are narrowed to allow the closely-wound region 42 to be bent at an appropriate position.

When the closely-wound region 42 is bent while the total length is maintained by the outer tube 36, the sparsely-wound portion 54 buffers the extension of the flexible tube 32 in the direction along the longitudinal axis L that is caused by the extension of the closely-wound portion 52 in the direction along the longitudinal axis L in the axial direction of the flexible tube 32. Accordingly, the sparsely-wound portion 54 of the closely-wound region 42 cancels the extension of the flexible tube 32 in the direction along the longitudinal axis L. Therefore, the presence of the sparsely-wound portion 54 in addition to the closely-wound portion 52 allows the closely-wound region 42 to bend smoothly in a state where the characteristics of the closely-wound portion 52 with high spring characteristics against the sparsely-wound portion 54 is maintained. Furthermore, the resiliency based on the tight contact force of the closely-wound portion 52 allows the closely-wound region 42 to return to an almost straight state from the bent state while the total length is maintained by the outer tube 36.

Not only when the external force is applied to the closely-wound portion 52 of the closely-wound region 42, but also when it is applied to the sparsely-wound portion 54 can the closely-wound region be bent while the sparsely-wound portion 54 receiving the external force and the other sparsely-wound portions 54 function a buffer.

It is preferable that the entire sparsely-wound region 44 is formed in the same manner as the sparsely-wound portion 54 of the closely-wound region 42. Therefore, when an external force is applied from a direction departing from the longitudinal axis L, the sparsely-wound region 44 is bent easier than when an external force is applied to the closely-wound region 42, and is more difficult to return to an approximately straight state in comparison to the closely-wound region 42. In the same manner as the sparsely-wound portion 54 of the closely-wound region 42, the sparsely-wound region 44 can also function as a buffer.

Figure 2B:
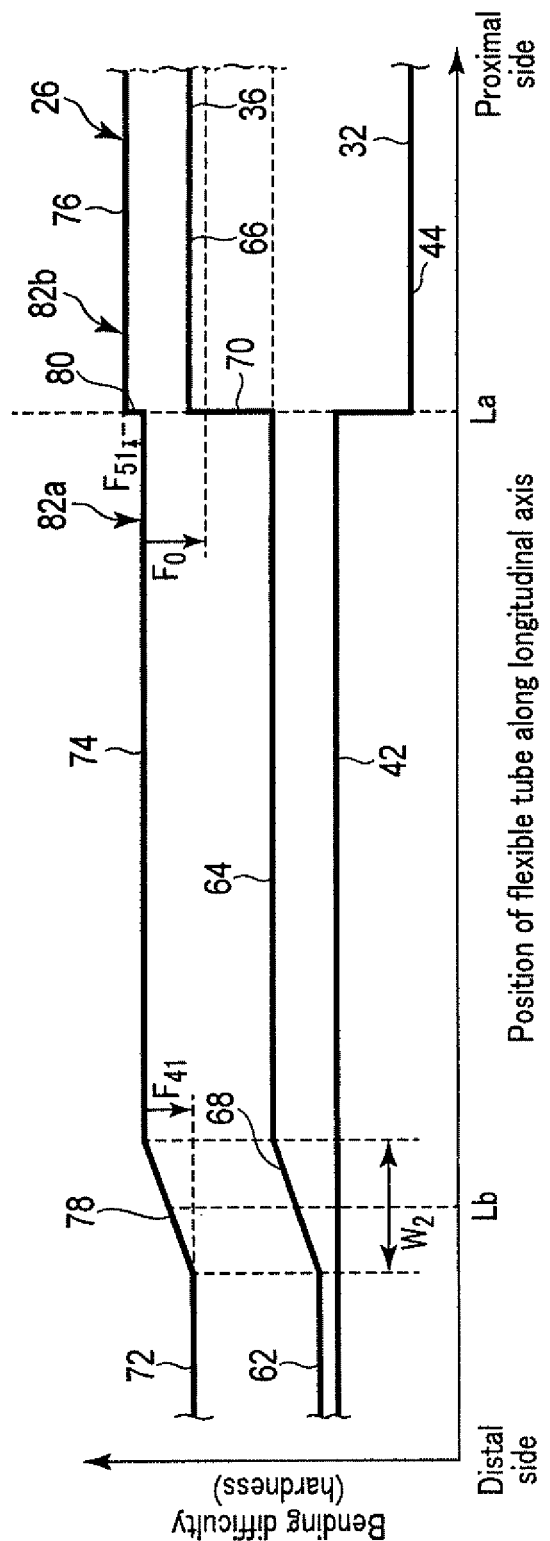
FIG. 2B is a schematic view showing a bending difficulty with respect to a position along a longitudinal axis of a helical tube and an outer tube of the flexible tube shown in FIG. 2A, together with a bending difficulty of the flexible tube obtained by adding the bending difficulties of the helical tube and the outer tube together by a principle of superposition.

As shown in FIG. 2A and FIG. 2B, the outer tube 36 includes a first outer layer 62 which covers the distal side of the closely-wound region 42, a second outer layer 64 which covers the proximal side of the closely-wound region 42, and a third outer layer 66 which covers the outer side of the sparsely-wound region 44 of the helical tube 32 of the flexible tube 26. To simplify the explanation, the bending difficulty in each region of the first to third outer layers 62, 64, and 66 will each be assumed as constant. The bending difficulty of the first outer layer 62 is less than the bending difficulty of the second outer layer 64. The bending difficulty of the second outer layer 64 is less than the bending difficulty of the third outer layer 66.

The outer tube 36 of the flexible tube 26 further includes a fourth outer layer 68 that is formed at a portion between the first outer layer 62 and the second outer layer 64 that respectively covers the closely-wound region 42, and a fifth outer layer (first flexible varying portion) 70 that is arranged continuously between the proximal end of the closely-wound region 42 and the distal end of the sparsely-wound region 44 and covers a portion between the proximal end of the closely-wound region 42 and the distal end of the sparsely-wound region 44 (outer side of a boundary position of the closely-wound portion 52 and the sparsely-wound portion 54). The bending difficulty of the fourth and fifth outer layers 68 and 70 is assumed to change along the axial direction. Here, to simplify the explanation, the bending difficulty of the fourth and fifth outer layers 68 and 70 is assumed to change linearly. Therefore, the fourth outer layer 68 is formed so that the bending difficulty (hardness) gradually increases from the distal side towards the proximal side of the longitudinal axis L between the proximal end of the first outer layer 62 and the distal end of the second outer layer 64. The fifth outer layer 70 is formed so that the bending difficulty drastically increases from the distal side towards the proximal side of the longitudinal axis L between the proximal end of the second outer layer 64 and the distal end of the third outer layer 66. A length (width) W2 of the fourth outer layer 68 along the longitudinal axis L is preferred to be between, for example, about a few centimeters and ten centimeters. Therefore, the length of a fourth flexible portion 78 along the longitudinal axis L explained later on is also defined as being similar to the length W2 of the fourth outer layer 68 along the longitudinal axis L. The fifth outer layer 70 is formed along the longitudinal axis L for only a minimal length (for example, a few millimeters).

The first to fifth outer layers 62, 64, 66, 68, and 70 are made of an appropriate resin material that suppresses extension and contraction in the direction of the longitudinal axis L and are integrated by, for example, extrusion molding. The resin material is preferred to be heat- and chemical-resistant and is formed of a material that can be repeatedly cleaned and sterilized. The resin material is also preferred to be electrically insulative (non-conductive).

When an external force is applied from a direction departing from the longitudinal axis L such as a direction perpendicular to the longitudinal axis L of the outer tube 36, the bending difficulty (hardness against bending) and the resiliency (easiness of returning to an approximately straight state from a bent state) of the outer tube 36 can be appropriately set by changing, for example, the mixture of an easily bent first resin material and a second resin material which is more difficult to bend in comparison to the first resin material. That is, the bending difficulty and resiliency of the outer tube 36 can be set appropriately between the bending difficulties and resiliencies of the first resin material and the second resin material. The number of substances to be mixed as the outer tube 36 resin material is not particularly limited.

The closely-wound region 42 of the helical tube 32 and the first outer layer 62 of the outer tube 36 cooperate with each other to form a first flexible portion 72. The closely-wound region 42 of the helical tube 32 and the second outer layer 64 of the outer tube 36 cooperate with each other to form a second flexible portion 74. The sparsely-wound region 44 of the helical tube 32 and the third outer layer 66 of the outer tube 36 cooperate with each other to form a third flexible portion 76. The closely-wound region 42 of the helical tube 32 and the fourth outer layer 68 of the outer tube 36 cooperate with each other to form a fourth flexible portion (flexible varying portion) 78. The boundary position of the proximal end of the closely-wound region 42 and the distal end of the sparsely-wound region 44 of the helical tube 32 and the fifth outer layer 70 of the outer tube 36 cooperate with each other to form a fifth flexible portion (flexible varying portion) 80.

As shown in FIG. 2B, generally, the bending difficulty of the first flexible portion 72 can be regarded as the sum of the bending difficulty of the closely-wound region 42 and the first outer layer 62 arranged radially outward in sequence from the longitudinal axis L. As mentioned above, the resiliency of the closely-wound region 42 is exhibited by the tight contact force between the adjacent parts of the wire member 32a. The resiliency of the first outer layer 62 is exhibited by the fabric itself of the outer tube 36. The resiliency of the first flexible portion 72 can generally be regarded as the sum of the resiliency of the closely-wound region 42 and the first outer layer 62 arranged radially outward in sequence from the longitudinal axis L. Each of the bending difficulty and resiliency of the first flexible portion 72 is essentially constant.

The bending difficulty of the second flexible portion 74 can generally be regarded as the sum of the bending difficulty of the closely-wound region 42 and the second outer layer 64 arranged radially outward in sequence from the longitudinal axis L. The resiliency of the second flexible portion 74 can generally be regarded as the sum of the resiliency of the closely-wound region 42 and the second outer layer 64 arranged radially outward in sequence from the longitudinal axis L. Each of the bending difficulty and resiliency of the second flexible portion 74 is essentially constant.

From a microscopic point of view, the bending difficulty and resiliency of the first and the second flexible portions 72 and 74 vary depending upon whether the position includes the closely-wound portions 52, or the position includes the sparsely-wound portions 54. However, from a macroscopic point of view, that is, when considering the entirety of the first and the second flexible portions 72 and 74 where the closely-wound region 42 is covered with the outer tube 36, the bending difficulty and the resiliency are respectively essentially constant. When using the flexible tube 26, the user of the insertion apparatus 10 can regard the bending difficulty and resiliency of the first and second flexible portions 72 and 74 as being constant. This is attributable to the fact that the sparsely-wound portion 54 is shorter in comparison to the closely-wound portion 52.

The bending difficulty of the third flexible portion 76 can generally be regarded as the sum of the bending difficulty of the sparsely-wound region 44 and the third outer layer 66 arranged radially outward in sequence from the longitudinal axis L. The resiliency of the third flexible portion 76 can generally be regarded as the sum of the resiliency of the sparsely-wound region 44 and the third outer layer 66. The bending difficulty and resiliency of the third flexible portion 76 are respectively essentially constant. In cooperation with the sparsely-wound region 44, the third flexible portion 76 is formed more difficult to bend than the first flexible portion 72, and as difficult to bend as or slightly more difficult to bend than the second flexible portion 74.

The bending difficulty of the fourth flexible portion 78 can generally be regarded as the sum of the bending difficulty of the closely-wound region 42 and the fourth outer layer 68 arranged radially outward in sequence from the longitudinal axis L. The resiliency of the fourth flexible portion 78 can generally be regarded as the sum of the resiliency of the sparsely-wound region 42 and the fourth outer layer 68. The bending difficulty and resiliency of the fourth flexible portion 78 are changed by the fourth outer layer 68 so as to increase essentially linearly from the distal end towards the proximal end.

The bending difficulty of the fifth flexible portion 80 can generally be regarded as the sum of the bending difficulty of the boundary position between the proximal end of the closely-wound region 42 and the distal end of the sparsely-wound region 44 and the bending difficulty of the fifth outer layer 70 arranged radially outward in sequence from, the longitudinal axis L. The resiliency of the fifth flexible portion 80 can generally be regarded as the sum of the resiliency of the boundary position between the proximal end of the closely-wound region 42 and the distal end of the sparsely-wound region 44, and the resiliency of the fifth outer layer 70.

It is desirable that an amount of change (rate of change) F41 of the bending difficulty of the fourth flexible portion 78 is larger than an amount of change F51 of the fifth flexible portion 80. It is desirable that the amount of change (rate of change) F51 of the bending difficulty of the fifth flexible portion 80 is as small as possible.

Here, at the boundary position between the closely-wound region 42 and the sparsely-wound region 44 of the helical tube 32, more specifically, at the proximal end of the closely-wound portion 52 at the most proximal end of the closely-wound region 42 and the distal end of the sparsely-wound region 44, the bending difficulty and the resiliency drastically change depending on the presence/absence of the tight contact force between the adjacent parts of the wire member 32a. This change affects the bending difficulty and the resiliency at the boundary position between the second flexible portion 74 and the third flexible portion 76. Therefore, the fifth outer layer 70 is arranged to serve as an adjuster to adjust the differences of the bending difficulty/easiness and resiliency of the fifth flexible portion 80 to be as small as possible at the boundary position between the closely-wound region 42 and the sparsely-wound region 44 of the helical tube 32. The fifth flexible portion 80 adjusts the composition of the outer tube 36 to approximate the bending difficulty/easiness thereof from the second flexible portion 74 to the third flexible portion 76. The fifth flexible portion 80 adjusts the bending difficulty/easiness of the fifth flexible portion 80 by the fifth outer layer 70, and makes the change in bending difficulty small between the second flexible tube 74 and the third flexible portion 76 to suppress drastic changes in the bending difficulty at the boundary between the second flexible portion 74 and the third flexible portion 76. In particular, the difference in the bending difficulty between the distal end and the proximal end of the fifth outer layer 70 is the same as or is larger than the difference in the bending difficulty between the proximal end of the closely-wound region 42 and the distal end of the sparsely-wound region 44. Therefore, the fifth flexible portion 80 makes the bending difficulty of the third flexible portion 76 the same as or more difficult to bend than the bending difficulty of the second flexible portion 74.

In the fourth flexible portion 78, the composition of the fourth outer layer 68 of the outer tube 36 is adjusted from the distal side towards the proximal side along the longitudinal axis L to approximate the bending difficulty (hardness)/bending easiness of the first flexible portion 72 to the second flexible portion 74.

The outer tube 36 defines the total length of the flexible tube 26 and is suppressed from extending/contracting in the axial direction of the longitudinal axis L. By pulling both ends of the helical tube 32 in opposite directions from each other along the longitudinal axis L, the helical tube 32 can be extended/contracted in the axial direction of the longitudinal axis L. Therefore, the outer tube 36 is considered to be formed less extensible than the closely-wound region 42 and the sparsely-wound region 44 of the helical tube 32. Accordingly, the outer tube 36 is assumed as being more difficult to bend than the helical tube 32. In other words, the outer tube 36 is assumed to have lower resiliency than the helical tube 32.

Since the second flexible portion 74 of the flexible tube 26 whose outer circumference of the helical tube 32 is covered by the outer tube 36 is to be inserted further into the passage by utilizing its resiliency, the second flexible portion 74 is desired to have a more appropriate flexibility and a higher resiliency in comparison to the third flexible portion 76. Therefore, it is desirable for the fifth flexible portion 80 to have more difficulty in bending than the second flexible portion 74, and to have the same difficulty in bending as, or more difficulty in bending than the third flexible portion 76. According to the present embodiment, the fifth outer layer 70 between the proximal end of the second outer layer 64 and the distal end of the third outer layer 66 is formed along the longitudinal axis L for only a minimal length (for example, a few millimeters). The fifth outer layer 70 drastically increases the bending difficulty (hardness) of the outer tube 36 from the second outer layer 64 up to the third outer layer 66. Therefore, compared to the amount of change F0 (refer to the dotted line in FIG. 2B) of the bending difficulty between the second flexible portion 74 and the third flexible portion 76 in the case where the second outer layer 64 and the third outer layer 66 have the same bending difficulty, the amount of change F51 (refer to the solid line in FIG. 25) from the proximal portion 82a of the second flexible portion 74 to the distal portion 82b of the third flexible portion 76 can be made smaller by the third outer layer 66 and the fifth outer layer 70 whose bending difficulty has been increased with respect to the second outer layer 64.

As mentioned above, it is also favorable for the first to the fifth flexible portions 72, 74, 76, 78, and 80 to include a common braid 34 between the helical tube 32 and the outer tube 36. The influence of the braid 34 on the bending difficulty of the flexible tube 26 with respect to the helical tube 32 and the outer tube 36 may be considered small enough to be ignored.

In the following, the operation of the insertion apparatus 10 of the present embodiment will be explained.

The user of the insertion apparatus 10 holds the grip section 14 and the first flexible portion 72 of the flexible tube 26. Then, the user inserts the insertion section 12 in the order of the distal rigid portion 22, the bending portion 24 and the flexible tube 26 into an appropriate narrow and curved passage, such as the large intestine. While operating the knobs 16a and 16b to appropriately bend the bending portion 24, the user changes the holding position of the flexible tube 26 gradually toward the proximal side, thereby allowing the insertion section 12 to be inserted further into the passage.

The first outer layer 62 of the outer tube 36 covering the closely-wound region 42 is bent easier than the second outer layer 64 covering the closely-wound region 42 in a similar manner. For this reason, the first flexible portion 72 is easier to bend in comparison to the second flexible portion 74. The fourth outer layer 68 of the outer tube 36 covering the closely-wound region 42 is more difficult to bend than the first outer layer 62 but is easier to bend than the second outer layer 64. Therefore, the fourth flexible portion 78 is harder to bend than the first flexible portion 72, but is easier to bend than the second flexible portion 74. Furthermore, by adjusting the fourth outer layer 68, the fourth flexible portion 78 is adjusted so that the bending difficulty gradually increases from the proximal end of the first flexible portion 72 towards the distal end of the second flexible portion 74.

Since the first flexible portion 72 of the flexible tube 26 whose outer circumference of the helical tube 32 is covered by the outer tube 36 is inserted further into the passage by utilizing its resiliency, the first flexible portion 72 is formed to bend moderately easier in comparison to the fourth flexible portion 78 and the second flexible portion 74. The fourth flexible portion 78 and the second flexible portion 74 are more difficult to bend than the first flexible portion 72; however, the bending difficulty of the fourth flexible portion 78 and the second flexible portion 74 is such as to be bent by an external force received from the inner circumference (inner wall) of the bending portion of the passage of the large intestine.

Since each of the first, second, and fourth flexible portions 72, 74, and 78 includes the closely-wound region 42 (in particular, a plurality of closely-wound portions 52), the resiliency is higher in comparison to the third flexible portion 76 including the sparsely-wound region 44. Therefore, it is easier for each of the first, second, and fourth flexible portions 72, 74, and 78 to return to the approximately straight state from the bent state in comparison to the third flexible portion 76. In other words, even if the flexible tube is bent at one of the positions of the first, second, and fourth flexible portions 72, 74, and 78, the tight contact force applied between the adjacent parts of the wire member 32a in the closely-wound region 42 of the first, second, and fourth flexible portions 72, 74, and 78 will cause the flexible tube to easily return to the approximately straight state.

When the insertion section 12 is inserted from an opening (for example, the anus) of a flexible passage, such as the large intestine, further into the passage (deep portion of the large intestine), an external force (including a force of gravity) is applied from the inner circumferential surface of the passage to the first, fourth, and second flexible portions 72, 78, and 74 from a direction departing from the direction along the longitudinal axis L of the flexible tube 26. In the case where the applied external force is smaller than the bending difficulty of the first flexible portion 72, the first flexible portion 72 is not bent and maintains a linear state. Likewise, in the case where the applied external force is smaller than the bending difficulty of the fourth flexible portion 78, the fourth flexible portion 78 is not bent and is inserted into the passage while maintaining the linear state. Likewise, in the case where the applied external force is smaller than the bending difficulty of the second flexible portion 74, the second flexible portion 74 is not bent and is inserted into the passage while maintaining the linear state.

If the external force (including the force of gravity) applied from the inner circumferential surface of the passage exceeds the bending difficulty of the first flexible portion 72, the first flexible portion 72 begins to bend from the essentially linear state. That is, the first flexible portion 72 is bent from the essentially linear state.

Since the second flexible portion 74 is formed to be bent appropriately by the external force from the passage such as the large intestine, and the fourth flexible portion 78 is formed to be bent easier after the first flexible portion 72, the large intestine may be prevented from receiving an excessive load. The bending difficulty at the fourth flexible portion 78 is gradually increased from the distal side to the proximal side thereof, thereby allowing the fourth flexible portion 78 to make the difference in bending easiness gentle between the first flexible portion 72 and the second flexible portion 74. Therefore, in the case where the first flexible portion 72 is bent by an external force, the fourth flexible portion 78 is also bent easily by the external force.

The fourth flexible portion 78 has a higher resiliency in comparison to the first flexible portion 72. Therefore, the fourth flexible portion 78 more easily returns to the approximately straight state from the bent state in comparison with the first flexible portion 72. That is, even if the fourth flexible portion 78 is bent at any position thereof, the tight contact force applied between the adjacent parts of the wire member 32a in the closely-wound region 42 of the fourth flexible portion 78 allows the fourth flexible portion 78 to easily return to the approximately straight state.

For example, in the case of inserting the distal portion 12a of the insertion section 12 into the passage from, for example, the anus to a deep part of the large intestine, since the first flexible portion 72 can be easily bent, the first flexible portion 72 can be bent appropriately along the inner circumferential surface of the passage. The fourth flexible portion 78 and the second flexible portion 74 are also bent by the application of an external force exceeding the bending difficulty received from the inner circumferential surface of the passage. Thus, the insertion section 12, including the first flexible portion 72, the fourth flexible portion 78, and the second flexible portion 74, bends along the curve of the flexible passage such as the large intestine.

The fourth flexible portion 78 and the second flexible portion 74 have higher resiliency than the first flexible portion 72. The resiliency of the fourth flexible portion 78 and the second flexible portion 74 allows the fourth flexible portion 78 and the second flexible portion 74 to be easily returned to the approximately straight state from the bent state. Therefore, after the first flexible portion 72 passes a curve of the passage, the fourth flexible portion 78 and the second flexible portion 74 utilize their resiliency to make the curved portion of the passage essentially linear. After the fourth flexible portion 78 and the second flexible portion 74 are bent, the insertion section 12 is pulled a little so that the external force applied to the fourth flexible portion 78 and the second flexible portion 74 is reduced. In this manner, the fourth flexible portion 78 and the second flexible portion 74 are allowed to easily exhibit their resiliency. Because of this, a passage having a small bending radius, such as the sigmoid colon, can be made essentially linear. Since the first flexible portion 72 is also resilient, it returns to an approximately straight state. In this manner, the distal end 12a of the insertion section 12 can be inserted into a deep portion of the passage.

After the first flexible portion 72, the fourth flexible portion 78, and the second flexible portion 74 are bent appropriately in sequence and pass the curve of the passage, the passage is made essentially linear by the resiliency of the first flexible portion 72, the fourth flexible portion 78, and the second flexible portion 74.

In this manner, the first flexible portion 72, the fourth flexible portion 78, and the second flexible portion 74 of the flexible tube 26 of the insertion section 12 are appropriately bent in response to the external force applied from the inner circumferential surface of the passage, and, while making the passage essentially linear by the resiliency of the second flexible portion 74, the distal portion 12a of the insertion section 12 is made to move further into the passage.

The bending difficulty of the fourth flexible portion 78 changes gently from the first flexible portion 72 up to the second flexible portion 74. Therefore, when the user pushes the distal end of the insertion section 12 further into the large intestine by gripping the second flexible portion 74, the force acting on the second flexible portion 74 is positively transmitted to the first flexible portion 72 through the fourth flexible portion 78. At this time, when an external force exceeding the bending difficulty is applied to the fourth flexible portion 78, the fourth flexible portion 78 is bent appropriately.

Let us assume that the distal portion 12a of the insertion section 12 is inserted further into the passage, and the proximal end of the second flexible portion 74 of the flexible tube 26 stops short of entering (outside the body) the opening (the anus) of the passage. More specifically, let us assume that the proximal end of the second flexible portion 74 is in the vicinity of the opening (the anus) of the passage. If an affected portion is at a position further into the passage (deep portion), the user holds the third outer layer 66 of third flexible portion 76 to push the insertion section 12 into the passage, and moves the distal portion 12a of the insertion section 12 further into the passage. At this time, the fifth flexible portion 70 suppresses the occurrence of a drastic change in the bending difficulty (hardness) of the flexible tube 26 at the boundary of the second flexible portion 74 and the third flexible portion 76. That is, the bending difficulty of the flexible tube 26, indicated by a solid line in FIG. 2B, has the change in the bending difficulty between the second flexible portion 74 and the third flexible portion 76 becoming smaller in comparison to the bending difficulty of the flexible tube of when the third outer layer is the same as the second outer layer, indicated by a dotted line. Therefore, by adjusting the bending difficulty of the outer tube 36 by the fifth outer layer 70, an extreme difference in the bending difficulty along the longitudinal axis L is suppressed from occurring between the second flexible portion 74 and the third flexible portion 76.

Therefore, the portion from the proximal end position of the second flexible portion 74 to the proximal side of the flexible tube 26 is suppressed as much as possible from deflecting by buckling. Here, when the insertion section 12 is pushed further into the passage, the transmission of force between the position of the third flexible portion 76 held by the user and the proximal portion of the second flexible portion 74 is performed favorably in comparison to the flexible tube in the case where the third outer layer has the same bending difficulty as the second outer layer. That is, the force that the user applies when the third flexible portion 76 of the flexible tube 26 is pushed along the longitudinal axis L is reliably transmitted from its position to the distal end 26a of the first flexible portion 72 through the third flexible portion 76, the second flexible portion 74, and the fourth flexible portion 78.

By arranging the fifth flexible portion 80 between the second flexible portion 74 and the third flexible portion 76, even if an advancing force is applied along the longitudinal axis L at any position from the proximal end position of the second flexible portion 74 to the proximal side of the flexible tube 26, deflecting (buckling) at such position can be suppressed. Therefore, the amount of operating force at the third flexible portion 76 held by the user of the insertion apparatus 10 is easily transmitted from the held position to the distal end 26a of the flexible tube 26 (the distal end of the first flexible portion 72), and the flexible tube 26 can be easily inserted further into the passage. In other words, the distal end 12a of the insertion section 12 can be easily inserted further into the passage.

As explained above, the insertion apparatus 10 according to the present embodiment may be considered as follows.

The bending difficulty/bending easiness between the proximal end of the closely-wound portion 52 on the most proximal side of the closely-wound region 42 and the distal end of the sparsely-wound region 44 of the helical tube 32 changes significantly. In a similar manner as the outer tube 36 of the present embodiment, by adjusting the bending difficulty of the second, third, and fifth outer layers 64, 66, and 70, that is, the bending difficulty of the fifth outer layer 70, in particular, the fifth flexible portion 80 between the proximal end of the second flexible tube 74 and the distal end of the third flexible tube 76 reduces the difference in the bending difficulty/bending easiness therebetween. Therefore, by adjusting the bending difficulty of the third and fifth outer layers 66 and 70 with respect to the second outer layer 64, when the user holds the third flexible portion 76 and pushes the distal end 12a of the insertion section 12, that is, the distal end 26a of the flexible tube 26, further into the passage, the force of pushing against the passage can be more easily transmitted from the third flexible portion 76 towards the distal end 26a of the first flexible portion 72 of the flexible tube 26. Accordingly, the deflecting (buckling) at the boundary position between the distal end of the third flexible portion 76 and the proximal end of the second flexible portion 74, in particular at the distal portion of the third flexible portion 76, can be prevented. In this manner, the fifth flexible portion 80 functions as a force transmission part and a bending suppression part.

Through the fifth flexible portion 80, the third flexible portion 76 is formed to be as difficult to bend as, or more difficult to bend than the second flexible portion 74. Therefore, the third flexible portion 76 is difficult to bend even by the force applied by the user when pushing the third flexible portion 76 of the flexible tube 26 along the longitudinal axis L. In this manner, the operation of the user pushing the third flexible portion 76 of the flexible tube 26 along the longitudinal axis L allows the force to be transmitted to the second flexible portion 74 without the third flexible portion 76 being bent.

Furthermore, by arranging the closely-wound region 42 of the helical tube 32 at the first, second, and fourth flexible portions 72, 74, and 78 on the distal side of the flexible tube 26, resiliency can be exhibited while exhibiting favorable bendability. Therefore, the insertion section 12 is capable of bending in accordance with a curve of the flexible passage, such as the large intestine, and, after passing the curve of the passage, being inserted into a deep part of the passage by utilizing the resiliency (the property of the bent flexible tube 26 that tends to return to the linear state) of the flexible tube 26 to make the curve of the passage essentially linear. As described above, when being inserted, the flexible tube 26 of the present embodiment is capable of making the passage essentially linear more easily than a flexible tube with low resiliency.

Therefore, the present embodiment is capable of providing a flexible tube 26 that can be easily inserted from the anus into a winding passage such as a deep part close to the appendix of the large intestine, from a partly inserted state, and can also provide an insertion apparatus 10 having such flexible tube 26.

Incidentally, the large intestine is a long organ having a number of curves. When the insertion section 12 of the insertion apparatus 10 is inserted into the large intestine, the flexible tube 26 needs to bend in accordance with the curves of the intestine. However, if the insertion section 12 is simply pushed in accordance with the curves, the large intestine may be excessively extended. In addition, a long time may be required for the insertion section 12 to pass through the large intestine with a number of curves and reach the appendix. If the large intestine is significantly extended, the insertion section 12 may not reach the appendix.

Therefore, as a technique for inserting the insertion section 12 into the large intestine, after an appropriate portion of the flexible tube 26 passes a curve of the large intestine, the resiliency of the flexible tube 26 (the property of the bent flexible tube 26 that tends to return to a linear state) is utilized to make the curve of the large intestine essentially linear. Accordingly, in order to facilitate the insertion of the insertion section 12 into the large intestine, it is effective to use a flexible tube 26 having high resiliency for making the large intestine essentially linear.

In the closely-wound region 42 of the flexible tube 26 of the present embodiment, the initial tension (tight contact force) is applied to the adjacent parts of the wire member 32*a* of the helical tube 32 along the longitudinal axis L. Therefore, resiliency can be enhanced, allowing the bent portion of the flexible tube 26 to easily return to an essentially straight state, and facilitating insertion into the large intestine.

In the present embodiment, in all, the outer tube 36 has been explained as being more difficult to bend than the flexible tube 26. However, as long as the flexible tube 26 can be appropriately bent, a part of the helical tube 32 may be more difficult to bend than a part of the outer tube 36. Furthermore, as long as the flexible tube 26 can be appropriately bent, in all, the helical tube 32 may be more difficult to bend than the outer tube 36.

In the following, the second embodiment will be explained using FIG. 3. The present embodiment is a modified example of the first embodiment, in which, to omit detailed explanations, the same symbols as those in the first embodiment will be applied whenever possible to the same members or the members with the same functions as those explained in the first embodiment.

Figure 3:
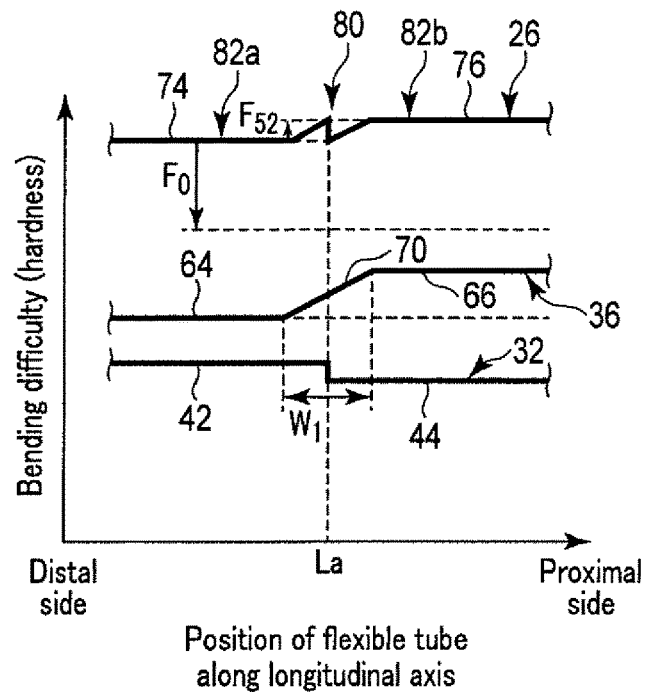
FIG. 3 is a schematic view showing a bending difficulty with respect to a position along a longitudinal axis of a helical tube and an outer tube of a flexible tube of an insertion section of an endoscope according to the second embodiment, together with a bending difficulty of the flexible tube obtained by adding the bending difficulties of the helical tube and the outer tube together by a principle of superposition.

As shown in FIG. 3, the fifth outer layer 70 of the outer tube 36 is formed striding over the proximal portion of the closely-wound portion 52 on the most proximal side of the closely-wound region 42 and the distal portion of the sparsely-wound region 44. That is, the fifth outer layer 70 covers the outer side including the boundary position of the proximal end of the closely-wound region 42 and the distal end of the sparsely-wound region 44. For example, a length (width) W1 of the fifth outer layer 70 along the longitudinal axis L is preferred to be between, for example, about a few ten millimeters and hundred millimeters. Therefore, the length of a fifth flexible portion 80 along the longitudinal axis L is also defined to be the same length as the length W1 of the fifth outer layer 70 along the longitudinal axis L. The fifth outer layer 70 is formed difficult to bend as it moves on from the distal side to the proximal side thereof.

Even if the fifth outer layer 70 is formed in this manner, similar to what has been explained in the first embodiment, when compared to the amount of change F0 (refer to the dotted line in FIG. 3) of the bending difficulty between the second flexible portion 74 and the third flexible portion 76 in the case where the second outer layer 64 and the third outer layer 66 have the same bending difficulty, the amount of change F52 (refer to the solid line in FIG. 3) from the proximal portion 82*a* of the second flexible portion 74 to the distal portion 82*b* of the third flexible portion 76 can be made smaller by the third outer layer 66 and the fifth outer layer 70 whose bending difficulty has been increased with respect to the second outer layer 64.

Therefore, when the insertion section 12 is pushed further into the passage, the transmission of force between the position of the third flexible portion 76 held by the user and the proximal portion of the second flexible portion 74 is favorably performed in comparison to the flexible tube in the case where the third outer layer has the same bending difficulty as the second outer layer. Accordingly, a portion towards the proximal side of a boundary between the closely-wound region 42 and the sparsely-wound region 44 of the flexible tube 26 can be suppressed from being deflected as much as possible. That is, the force which the user applies when pushing the third flexible portion 76 of the flexible tube 26 along the longitudinal axis L is reliably transmitted to the distal end 26*a* of the first flexible portion 72 of the flexible tube 26.

In particular, through the fifth flexible portion 80, the third flexible portion 76 is formed to be as difficult to bend as, or more difficult to bend than the second flexible portion 74. Therefore, the third flexible portion 76 is difficult to bend even by the force applied by the user when pushing the third flexible portion 76 of the flexible tube 26 along the longitudinal axis L. In this manner, the operation of the user pushing the third flexible portion 76 of the flexible tube 26 along the longitudinal axis L allows the force to be transmitted to the second flexible portion 74 without the third flexible portion 76 being bent.

In the following, the third embodiment will be explained using FIG. 4. This embodiment is a modification of the first and second embodiments. To omit detailed explanations, the same members or the members having the same functions as those of the members of the first and second embodiments are identified by the same reference symbols as those used for those embodiments whenever possible.

Figure 4:
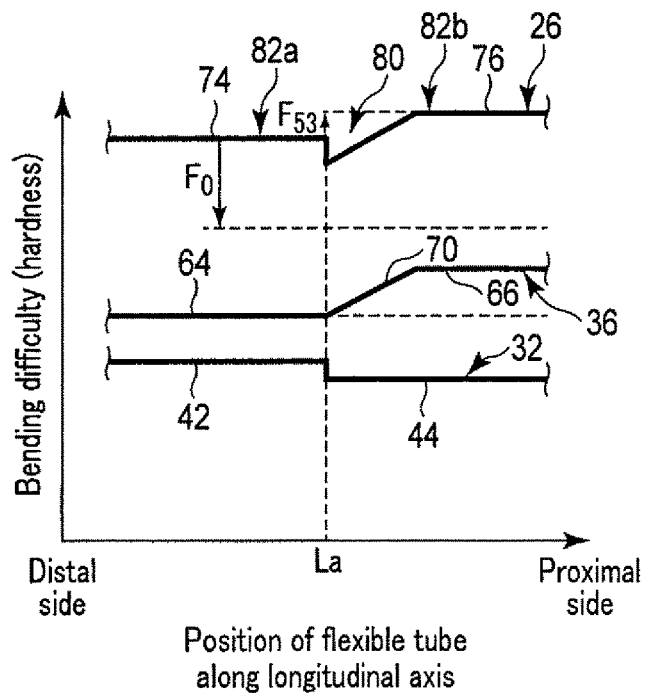
FIG. 4 is a schematic view showing a bending difficulty with respect to a position along a longitudinal axis of a helical tube and an outer tube of a flexible tube of an insertion section of an endoscope according to the third embodiment, together with a bending difficulty of the flexible tube obtained by adding the bending difficulties of the helical tube and the outer tube together by a principle of superposition.

As shown in FIG. 4, the fifth outer layer 70 is formed between the proximal end of the closely-wound portion 52 on the most proximal side of the closely-wound region 42 and the distal portion of the sparsely-wound region 44. That is, the boundary between the proximal end of the second outer layer 64 and the distal end of the fifth outer layer 70 is on the outer circumference of the boundary position of the proximal end of the closely-wound region 42 and the distal end of the sparsely-wound region 44. The fifth outer layer 70 is formed difficult to bend as it moves on from the distal side to the proximal side thereof. That is, in the fifth outer layer 70, the bending difficulty gradually increases from the proximal end of the second outer layer 64 towards the distal end of the third outer layer 66.

Even if the fifth outer layer 70 is formed in this manner, similar to what has been explained in the first embodiment, when compared to the amount of change F0 (refer to the dotted line in FIG. 4) of the bending difficulty between the second flexible portion 74 and the third flexible portion 76 in the case where the second outer layer 64 and the third outer layer 66 have the same bending difficulty, the amount of change F53 (refer to the solid line in FIG. 4) from the proximal portion 82*a* of the second flexible portion 74 to the distal portion 82*b* of the third flexible portion 76 can be made smaller by the third outer layer 66 and the fifth outer layer 70 whose bending difficulty has been increased with respect to the second outer layer 64. In particular, through the fifth flexible portion 80, the third flexible portion 76 is formed to be as difficult to bend as, or more difficult to bend than the second flexible portion 74.

Therefore, when the insertion section 12 is pushed further into the passage, the transmission of force between the position of the third flexible portion 76 held by the user and the proximal portion of the second flexible portion 74 is performed favorably in comparison to the flexible tube where the third outer layer has the same bending difficulty as the second outer layer. Accordingly, a portion from a boundary between the closely-wound region 42 and the sparsely-wound region 44 towards the proximal side of the flexible tube 26 can be suppressed from being deflected as much as possible. That is, the force which the user applies when pushing the second flexible portion 74 of the flexible tube 26 along the longitudinal axis L is reliably transmitted to the distal end 26*a* of the first flexible portion 72 of the flexible tube 26.

In the following, the fourth embodiment will be explained using FIG. 5. This embodiment is a modification of the first to third embodiments. To omit detailed explanations, the same members or the members having the same functions as those of the members of the first to third embodiments are identified by the same reference symbols as those used for those embodiments whenever possible.

As shown in FIG. 5, the fifth outer layer 70 is formed between the distal end of the sparsely-wound region 44 and the proximal portion of the closely-wound portion 52 on the most proximal side of the closely-wound region 42. That is, the boundary between the distal end of the third outer layer 66 and the proximal end of the fifth outer layer 70 is on the outer circumference of the boundary position of the proximal end of the closely-wound region 42 and the distal end of the sparsely-wound region 44. The fifth outer layer 70 is formed difficult to bend as it transitions from the distal side to the proximal side thereof.

Even if the fifth outer layer 70 is formed in this manner, similar to what has been explained in the first embodiment, when compared to the amount of change F0 (refer to the dotted line in FIG. 5) of the bending difficulty between the second flexible portion 74 and the third flexible portion 76 in the case where the second outer layer 64 and the third outer layer 66 have the same bending difficulty, the amount of change F54 (refer to the solid line in FIG. 5) from the proximal portion 82*a* of the second flexible portion 74 to the distal portion 82*b* of the third flexible portion 76 can be made smaller by the third outer layer 66 and the fifth outer layer 70 whose bending difficulty has been increased with respect to the second outer layer 64. In particular, through the fifth flexible portion 80, the third flexible portion 76 is formed to be as difficult to bend as, or more difficult to bend than the second flexible portion 74.

Therefore, when the insertion section 12 is pushed further into the passage, the transmission of force between the position of the third flexible portion 76 held by the user and the proximal portion of the second flexible portion 74 is carried out favorably in comparison to the flexible tube in the case where the third outer layer has the same bending difficulty as the second outer layer. Accordingly, a portion from a boundary between the closely-wound region 42 and the sparsely-wound region 44 towards the proximal side of the flexible tube 26 can be suppressed from being deflected as much as possible. That is, the force which the user applies when pushing the third flexible portion 76 of the flexible tube 26 along the longitudinal axis L is reliably transmitted to the distal end 26*a* of the first flexible portion 72 of the flexible tube 26.

In the following, the fifth embodiment will be explained using FIG. 6. This embodiment is a modification of the first to fourth embodiments. To omit detailed explanations, the same members or the members having the same functions as those of the members of the first to fourth embodiments are identified by the same reference symbols as those used for those embodiments whenever possible.

As shown in FIG. 6, the fifth outer layer 70 is formed so that its bending difficulty increases gradually, not linearly, but with a smooth curved surface, from the distal end towards the proximal end thereof. At the fifth outer layer 70, it is also suitable to change the bending difficulty in this manner. Therefore, the bending difficulty of the fifth flexible portion 80 increases gradually, not linearly, but in a smooth curved line, from the distal side towards the proximal side.

Even if the fifth outer layer 70 is formed in this manner, similar to what has been explained in the first embodiment, when compared to the amount of change F0 (refer to the dotted line in FIG. 6) of the bending difficulty between the second flexible portion 74 and the third flexible portion 76 in the case where the second outer layer 64 and the third outer layer 66 have the same bending difficulty, the amount of change F55 (refer to the solid line in FIG. 6) from the proximal portion 82*a* of the second flexible portion 74 to the distal portion 82*b* of the third flexible portion 76 can be made smaller by the third outer layer 66 and the fifth outer layer 70 whose bending difficulty has been increased with respect to the second outer layer 64. In particular, through the fifth flexible portion 80, the third flexible portion 76 is formed to be as difficult to bend as, or more difficult to bend than the second flexible portion 74.

In the same manner, it is also preferred that the fifth outer layer 70 explained in the second to fourth embodiments is also formed so that the bending difficulty gradually increases in a smooth curved line.

In the following, the sixth embodiment will be explained using FIG. 7. This embodiment is a modification of the first to fifth embodiments. To omit detailed explanations, the same members or the members having the same functions as those of the members of the first to fifth embodiments are identified by the same reference symbols as those used for those embodiments whenever possible.

Figure 7:
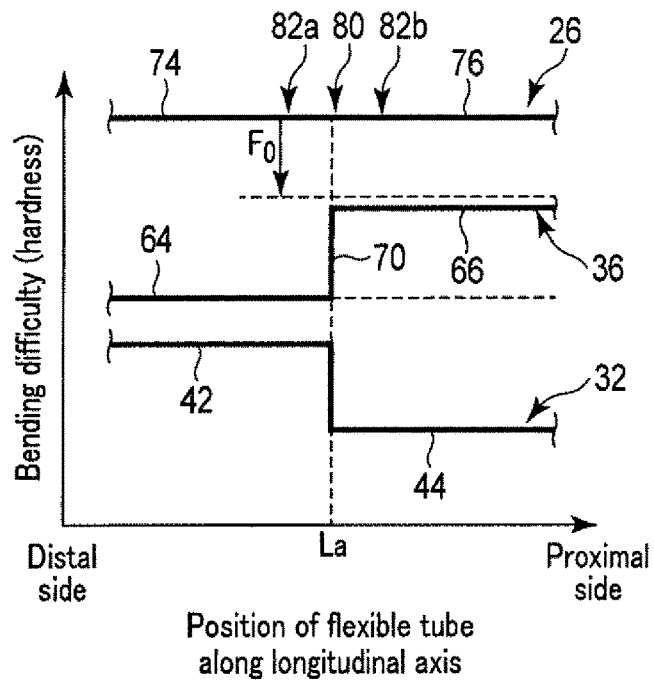
FIG. 7 is a schematic view showing a bending difficulty with respect to a position along a longitudinal axis of a helical tube and an outer tube of a flexible tube of an insertion section of an endoscope according to the sixth embodiment, together with a bending difficulty of the flexible tube obtained by adding the bending difficulties of the helical tube and the outer tube together by a principle of superposition.

As shown in FIG. 7, the fifth outer layer 70 is formed on the outer side of the boundary position between the proximal end of the closely-wound region 42 and the distal end of the sparsely-wound region 44 so that the bending difficulty drastically increases from the distal side to the proximal side along the longitudinal axis L. When the fifth outer layer 70 is formed in this manner, the bending difficulty of the fifth flexible portion 80 between the second flexible portion 74 and the third flexible portion 76 of the flexible tube 26 can be maintained in an essentially constant state. That is, through the fifth flexible portion 80, the third flexible portion 76 is formed to be as difficult to bend as the second flexible portion 74.

In the following, the seventh embodiment will be explained using FIG. 8. This embodiment is a modification of the first to sixth embodiments. To omit detailed explanations, the same members or the members having the same functions as those of the members of the first to sixth embodiments are identified by the same reference symbols as those used for those embodiments whenever possible.

Figure 8:
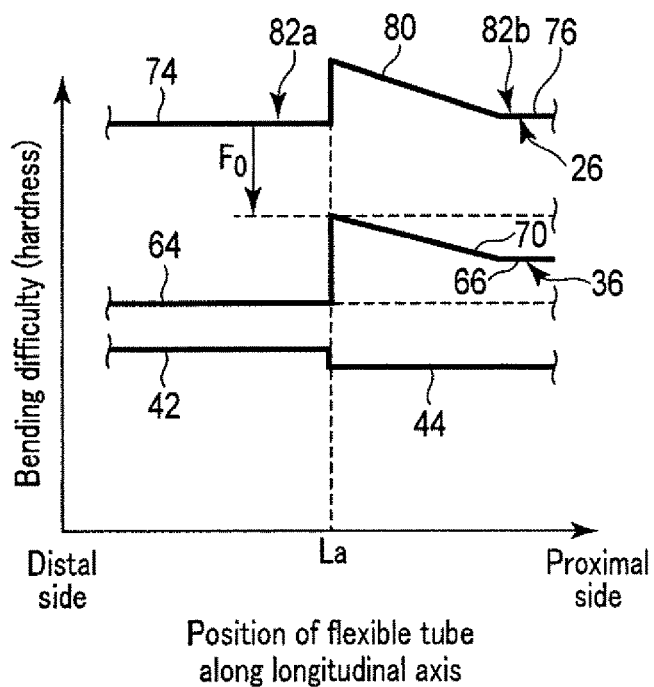
FIG. 8 is a schematic view showing a bending difficulty with respect to a position along a longitudinal axis of a helical tube and an outer tube of a flexible tube of an insertion section of an endoscope according to the seventh embodiment, together with a bending difficulty of the flexible tube obtained by adding the bending difficulties of the helical tube and the outer tube together by a principle of superposition.

As shown in FIG. 8, the fifth outer layer 70 is formed so that the bending difficulty increases drastically at the proximal end of the second outer layer 64 and gradually decreases towards the proximal side. The bending difficulty of the flexible tube 26 can be made to gradually decrease from the proximal end of the second flexible portion 74 towards the distal end of the third flexible portion 76. Through the fifth flexible portion 80, the third flexible portion 76 is formed to be as difficult to bend as, or more difficult to bend than the second flexible portion 74.

In the following, an eighth embodiment will be explained using FIG. 9A and FIG. 9B. This embodiment is a modification of the first to seventh embodiments. To omit detailed explanations, the same members or the members having the same functions as those of the members of the first to seventh embodiments are identified by the same reference symbols as those used for those embodiments whenever possible.

Figure 9A:
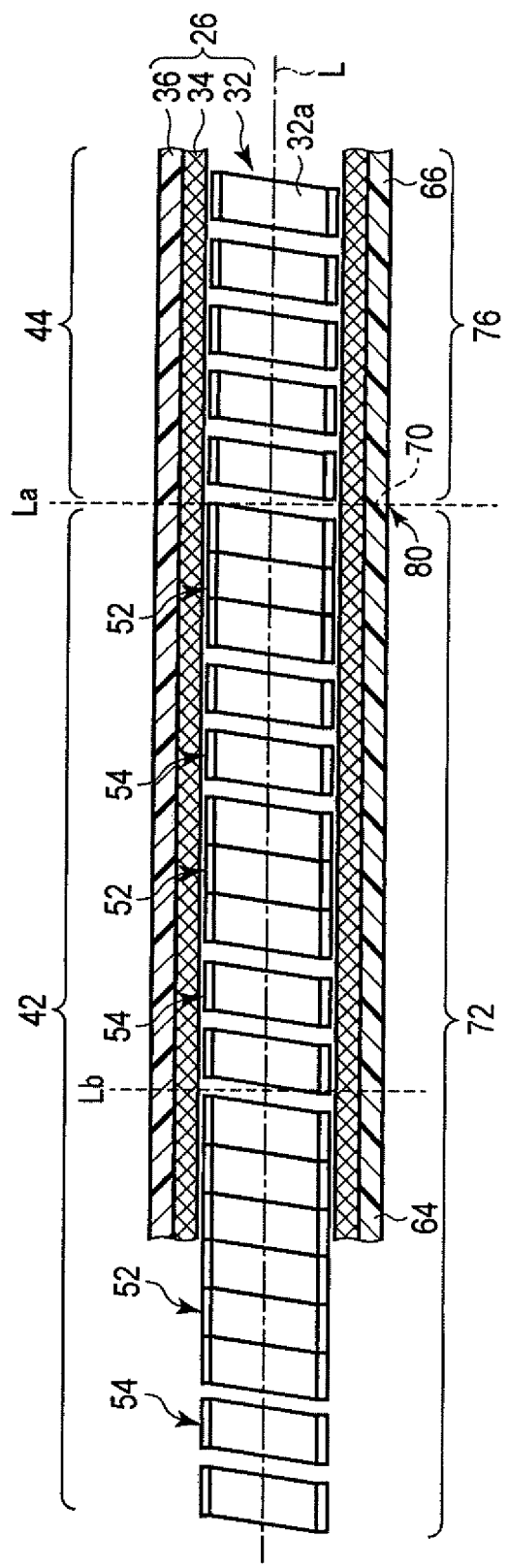
FIG. 9A is a schematic longitudinal sectional view of a part of a flexible tube of an insertion section of an endoscope according to the eighth embodiment.
Figure 9B:
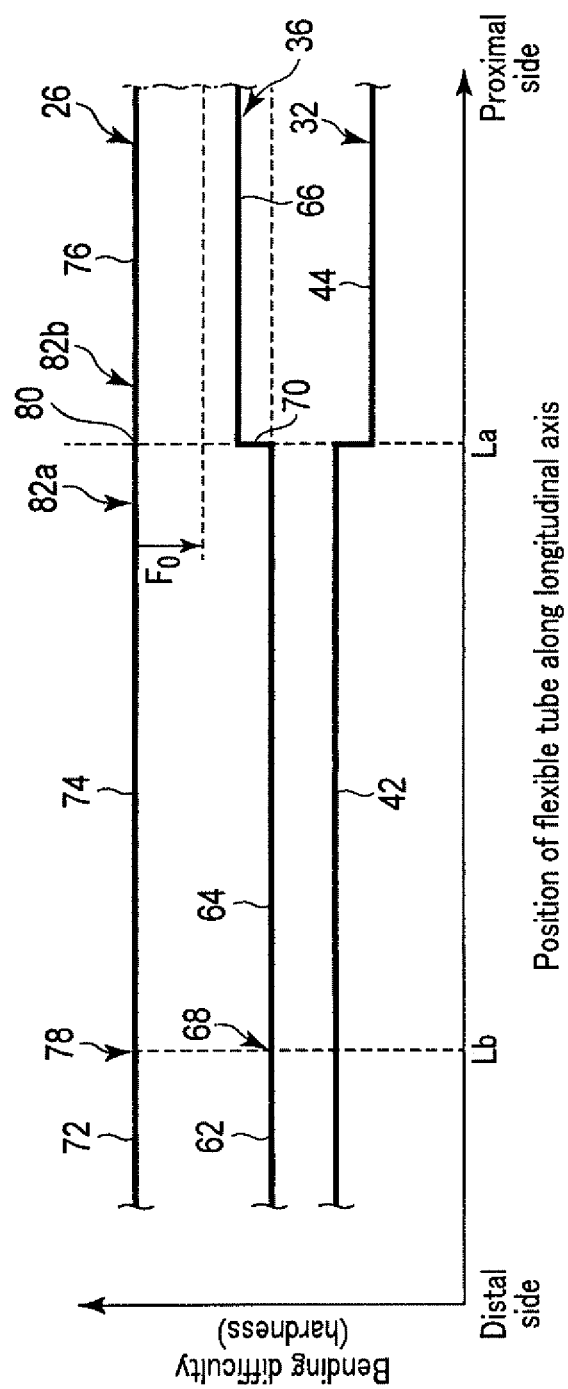
FIG. 9B is a schematic view showing a bending difficulty with respect to a position along a longitudinal axis of a helical tube and an outer tube of the flexible tube shown in FIG. 9A, together with a bending difficulty of the flexible tube obtained by adding the bending difficulties of the helical tube and the outer tube together by a principle of superposition.

In the present embodiment, as shown in FIG. 9A and FIG. 9B, the fifth flexible portion 80 at the boundary between the second and third flexible portions 74 and 76 is formed in the same manner as that explained in the first embodiment. It is also suitable to be formed in the same manner as explained in the second to seventh embodiments.

In the present embodiment, the first to fourth outer layers 62 and 68 are formed in the same manner as the second outer layer 64. That is, here, the flexible varying portion is removed, and the first flexible portion 72, the fourth flexible portion 78, and the second flexible portion 74 are formed to have the same bending difficulty and resiliency. It is also preferable that the flexible tube 26 is formed in the above manner.

Through the fifth flexible portion 80, the third flexible portion 76 is formed to be as difficult to bend as the second flexible portion 74.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube comprising:
   a closely-wound region which is arranged along a longitudinal axis defined by a distal end and a proximal end of the flexible tube, and which includes a closely-wound portion to which a tight contact force where adjacent parts of a wire member adjacent along the longitudinal axis come in a tight contact state with each other is applied;
   a sparsely-wound region which is arranged consecutively on a proximal side of the closely-wound region along the longitudinal axis, and which is formed so that the adjacent parts of the wire member adjacent along the longitudinal axis are separated from each other to be bent easier than the closely-wound region;
   a first outer layer which covers an outer side of the closely-wound region, and which forms a first flexible portion in cooperation with the closely-wound region;
   a second outer layer which is positioned closer to the proximal side than the first outer layer along the longitudinal axis, and which forms a second flexible portion which is more difficult to bend than the first flexible portion in cooperation with the closely-wound region;
   a third outer layer which covers an outer side of the sparsely-wound region, and which, in cooperation with the sparsely-wound region, forms a third flexible portion, the third flexible portion being more difficult to bend than the first flexible portion, and being as difficult to bend as the second flexible portion or more difficult to bend than the second flexible portion; and
   a fourth outer layer which is arranged consecutively between the second outer layer and the third outer layer to cover the outer side of a boundary position of the closely-wound region and the sparsely-wound region, the fourth outer layer being constructed such that a change in bending difficulty/bending easiness over a longitudinal distance of the boundary position is reduced compared to if the fourth outer layer was not present.

2. The flexible tube according to claim 1, wherein the fourth outer layer is more difficult to bend than the second outer layer, and is bent easier than the third outer layer.

3. The flexible tube according to claim 1, wherein the fourth outer layer covers an outer circumference including the boundary position.

4. The flexible tube according to claim 1, wherein a boundary between a proximal end of the second outer layer and a distal end of the fourth outer layer is on an outer circumference of a boundary position of the closely-wound region and the sparsely-wound region.

5. The flexible tube according to claim 1, wherein a boundary between a distal end of the third outer layer and a proximal end of the fourth outer layer is on an outer circumference of a boundary position of the closely-wound region and the sparsely-wound region.

6. The flexible tube according to claim 1, wherein a bending difficulty of the fourth outer layer increases from a proximal end of the second outer layer to a distal end of the third outer layer.

7. The flexible tube according to claim 1, wherein the first outer layer to the fourth outer layer are formed integrally.

8. The flexible tube according to claim 1, comprising a fifth outer layer on an outer circumference of the closely-wound region between the first outer layer and the second layer, the fifth outer layer having a bending difficulty that increases from a proximal end of the first layer to a distal end of the second outer layer.

9. The flexible tube according to claim 8, wherein the first outer layer to the fifth outer layer are formed integrally.

10. An insertion apparatus comprising the flexible tube according to claim 1.

* * * * *